United States Patent [19]
Delevalleé et al.

[11] Patent Number: 4,614,736
[45] Date of Patent: * Sep. 30, 1986

[54] NOVEL ANTI-INFLAMMATORY TREATMENT

[75] Inventors: Françoise Delevalleé, Vincennes; Roger Deraedt, Pavillons-sous-Bois; Simone Jouquey, Paris, all of France

[73] Assignee: Roussel Uclaf, Paris, France

[*] Notice: The portion of the term of this patent subsequent to May 7, 2002 has been disclaimed.

[21] Appl. No.: 718,175

[22] Filed: Apr. 1, 1985

[30] Foreign Application Priority Data

Apr. 3, 1984 [FR] France .................. 84 05222

[51] Int. Cl.$^4$ ................................ C07J 5/00
[52] U.S. Cl. ................ 514/179; 260/397.45
[58] Field of Search ............ 260/397.45; 514/179

[56] References Cited

U.S. PATENT DOCUMENTS 4,515,787  5/1985  Teutsch et al. ............ 260/397.45

*Primary Examiner*—Elbert L. Roberts
*Attorney, Agent, or Firm*—Bierman, Peroff & Muserlian

[57] ABSTRACT

A novel method of treating inflammation of the colon and rectum of warm-blooded animals comprising administering to the colon and rectum of warm-blooded animals an anti-inflammatorily effective amount of $9\alpha,11\beta$-dichloro-$16\alpha$-methyl-21-oxycarbonyldicyclohexylmethoxy-$\Delta^{1,4}$-pregnadiene-3,20-dione.

10 Claims, No Drawings

NOVEL ANTI-INFLAMMATORY TREATMENT

STATE OF THE ART

U.S. Pat. No. 4,353,899 describes the preparation of 9α,11β-dichloro-16α-methyl-21-oxycarbonyldicyclohexylmethoxy -$\Delta^{1,4}$-pregnadiene-3,20-dione and its "in loco" anti-inflammatory activity. The said compound is indicated in the patent as being inactive when orally administered which makes the compound particularly interesting for "in loco" administration by aerosol means due to the dissociation between the types of anti-inflammatory activity. The said patent indicates that the compound is, therefore, useful for the treatment of asthma, oedemas, dermatosis, pruritis and various forms of eczema and solar erythemas. U.S. Pat. No. 3.329.570 describes steroid compounds having oxycarbonyldioyclohexylmethoxy function in 21-position.

OBJECTS OF THE INVENTION

It is an objeot of the invention to provide a novel method of treating inflammatory conditions of the colon and rectum of warm-blooded animals, including humans.

This and other objects and advantages of the invention will become obvious from the following detailed description.

THE INVENTION

The novel method of the invention of treating inflammation of the colon and rectum of warm-blooded animals comprises administering to the colon and rectum of warm-blooded animals an anti-inflammatorily effective amount of 9α,11β-dichlo-16α-methyl-21-oxycarbonyldicyclohexylmethoxy-$\Delta^{1,4}$-pregnadiene-3,20-dione. The method of especially useful for treating inflammatory diseases of the colon and rectum. such as haemorrhagic rectocolitis and Crohn's disease. The usual daily dose is 0.01 to 1.25 mg/kg, preferably 0.06 to 0.6 mg/kg and most preferably 0.25 to 0.06 mg/kg, depending on the condition treated The anti-inflammatory compositions of the invention are comprised of an anti-inflammatorily effective amount of 9α,118β-dichloro-16α-methyl-21-oxycarbonyldicyclohexylmethoxy-$\Delta^{1,4}$-pregnadiene-3,20-dione and an inert pharmaceutical carrier capable of releasing the said compound in the colon and/or rectum. The com-positions may be in oral form such as tablets, dragees, capsules, granules, colic delitescent capsules such as those prepared by the method of French Pat. No. 2,471,186, and rectal forms such as enemas, dose-enemas, suppositories, foams and Scherrer rectal capsules prepared by the usual methods.

Examples of suitable inert pharmaceutical carriers are talc, lactose, starch and its derivatives, cellulose and its derivatives, polyvinyl-pyrrolidone, colloidal silica, the polyethylene-glycols, dicalcium phosphate, tricalcium phosphate, acrylic acid polymers, methacrylic acid-methacrylate polymers, gelatin, magnesium stearate, aqueous or non-aqueous vehicles, fatty substances of animal, vegetable or synthetic origin, paraffin derivatives, glycols, the various wetting, dispersing or emulsifying agents and preservatives.

The oral administration enables the active compound to traverse the greater part of the digestive tract without transformation and to reach the colon and rectum so as to effect the desired anti-inflammatory activity there. The preferred form is tablet, capsule, enema or suppository.

In the following examples there are described several preferred embodiments to illustrate the invention. However, it should be noted that the invention is not intended to be limited to the specific embodiments.

EXAMPLE 1

Capsules were prepared containing 10 mg of 9α,11β-dichloro-16α-methyl-21-oxycarbonyldicyclohexylmethoxy-$\Delta^{1,4}$-pregnadiene-3,20-dione and sufficient excipient for a final capsule weight of 120 mg.

EXAMPLE 2

Capsules were prepared containing 25 mg of 9α,11β-dichloro-16α-methyl-21-oxycarbonyldicyclohexylmethoxy-$\Delta^{1,4}$-pregnadiene-3,20-dione and sufficient excipient for a final capsule weight of 50 mg.

PHARMACOLOGICAL DATA

Male Sprague-Dawley rats weighing 200–250 g were sensi-tized by cutaneous application of an alcoholic solutinn of 2.5% dinitrochlorobenzene (DNCB). After choosing those animals present-ing on the 7th day a positive hypersensitivity, the test was carried out as follows: Every day for the three following days, there was administered by intra-rectal route 2 ml of a 2.5% solution of DNCB in an acetone-vaseline oil mixture and the same time, the test compound (product A) is administered by oral route. The animals were killed 24 hours after the last treatment and the severity of the ulcerous lesions was evaluated. To judge the possible systemic effects of the products, the thymus and the suprarenals were also removed. This test is a modification of the method described by NORRIS [Action of anti-colitic drugs on a guinea-pig model of immune colitis, Agents and Actions, Vol. 12, ½, p. 239–242 (1982)]. The following results were obtained.

|  | Dose mg/kg of product | % rats with ulcers | weight of thymus in mg | weight of suprarenals in mg |
| --- | --- | --- | --- | --- |
| Controls |  | 0 | 420 ± 24 | 40 ± 0.2 |
| DNCB |  | 72 | 349 ± 44 | 45 ± 1.6 |
| DNCB + Product A | 20 | 28 | 377 ± 24 | 42 ± 0.2 |
| DNCB + Product A | 50 | 14 | 345 ± 17 | 41 ± 1.5 |
| DNCB + Dexamethasone | 0.1 | 72 | 117 ± 6** | 30 ± 1.7 |
| DNCB + Prednisolone | 50 | 100 | 109 ± 11** | 31 ± 2.7 |

CONCLUSION

These results show that the oroduct A or 9α.118β-dichloro-16α-methyl-21-oxycarbonyldicyclohexylmethoxy-$\Delta^{1,4}$-pregnadiene-3,20-dione presented a clear activity in this model of immune rectocolitis without systemic effect. On the other hand, dexamethasone and prednisolone proved to be inactive against ulcerous lesions caused by DNCB but present a systemic activity as shown by the reduction of weight of the thymus and the suprarenals.

Various modifications of the method and compositions of the invention may be made without departing from the spirit or scope thereof and it is to be understood that the invention is intended to be limited only as defined in the appended claims.

What is claimed is:

1. A method of treating inflammation of the colon and rectum of warm-blooded animals comprising administering to the colon and rectum of warm-blooded animals an anti-inflammatorily effective amount of 9α,11β-dichloro-16α-methyl-21-oxycarbonyldicyclohexyl-methoxy-$\Delta^{1,4}$-pregnadiene-3,20-dione.

2. The method of claim 1 wherein the compound is administered orally.

3. The method of claim 2 wherein the compound is administered in a tablet.

4. The method of claim 2 wherein the compound is administered in a capsule.

5. The method of claim 1 wherein the compound is administered rectally.

6. The method of claim 5 wherein the compound is administered in a suppository.

7. The method of claim 5 wherein the compound is administered in an enema.

8. An anti-inflammatory composition comprising an anti-inflammatorily effective amount of 9α,11β-dichloro-16α-methyl-21-oxycarbonyldicyclohexylmethoxy-$\Delta^{1,4}$-pregnadiene-3,20-dione and an inert pharmaceutical carrier capable of releasing the said compound in the colon and/or rectum.

9. A composition of claim 6 in the form of a tablet or capsule.

10. A composition of claim 6 in the form of an enema or suppository.

* * * * *